United States Patent [19]
Rashman et al.

[11] Patent Number: 6,015,024
[45] Date of Patent: Jan. 18, 2000

[54] STETHOSCOPE HEAD WITH REMOVABLE BELLS

[75] Inventors: Richard Rashman, Los Angeles; Dennis Shick, Burbank, both of Calif.

[73] Assignee: Prestige Medical Corporation, Northridge, Calif.

[21] Appl. No.: 08/962,338

[22] Filed: Oct. 31, 1997

[51] Int. Cl.[7] .................................................. A61B 7/02
[52] U.S. Cl. .......................................... 181/131; 181/137
[58] Field of Search .................................... 181/131, 137

[56] References Cited

U.S. PATENT DOCUMENTS

| | | | |
|---|---|---|---|
| D. 401,337 | 11/1998 | Rashman . | |
| 965,174 | 7/1910 | Fuchs | 181/131 |
| 3,215,224 | 11/1965 | Machlup | 181/131 |
| 4,502,562 | 3/1985 | Nelson . | |
| 4,823,906 | 4/1989 | Bagriel | 181/137 |
| 5,498,841 | 3/1996 | Allen | 181/137 |
| 5,512,840 | 5/1996 | Selinger | 181/131 |

FOREIGN PATENT DOCUMENTS 101924  10/1997  Japan .

*Primary Examiner*—Khanh Dang
*Attorney, Agent, or Firm*—Blakely Sokoloff Taylor & Zafman

[57] ABSTRACT

A stethoscope head with multiple removable diaphragm structures and bell components for adapting the stethoscope for use with infants or adults, or on sites having less skin area, such as between the ribs is described. The bell components further include a wider rim than a conventional rim for better acoustically sealing the rim to the skin of the patient's body above the site to be auscultated. Further, the bell component is metallic providing for better sound conductivity than a non-metallic bell component. A non-metallic ring is disposed on the rim to better acoustically seal the rim with the skin of the patient's body and further, provide comfort to the patient since the non-metallic ring is not as cold as the metallic rim. The bell component includes a thick body to exclude external noises from interfering with the sound to be auscultated.

17 Claims, 2 Drawing Sheets

STETHOSCOPE HEAD WITH REMOVABLE BELLS

BACKGROUND OF THE INVENTION

This invention relates generally to stethoscope heads, particularly, to bell components that adapt the stethoscope head for use on infants or adults and in locations of smaller skin areas. In general, a head of a stethoscope is typically a dual head type consisting of a diaphragm on one side and a bell on the other. The diaphragm is suitable for detecting low frequency range sounds associated with diastolic and third heart sounds. The bell is suitable for detecting higher frequency range sounds such as those which signify murmurs. Typically, for the best detection of sounds, it is desirable to acoustically seal the rim of the bell with the skin of the patient's body above the site to be auscultated. For this reason, a bell suitable for use with an adult may not be suitable for use with an infant. Further, the region between the ribs is narrow, and therefore, an adult size bell might be too large to be used in such a location. One method of resolving this problem is using a stethoscope head with detachable diaphragm structures and bell components that adapt to the particular use required.

An example of a stethoscope with such an adaptable stethoscope head is known as the "Sprague". The Sprague stethoscope has a configuration which includes a chest piece with a drum and a stem, and removable diaphragm structures and bell components that attach to the drum. The diaphragm structures and bell components come in various sizes and are typically screwed onto the drum. While such configuration improves the detection of sounds, it is desirable to further acoustically seal the rim of the bell to the skin of the patient's body for the best detection of sounds. Moreover, the bell components may be made of plastic which is a poor conductor of sounds detected. Accordingly, what is needed is a stethoscope with a stethoscope head, in particular, bell components that provide excellent sound conductivity and a desirable acoustic seal with the skin of the patient's body.

BRIEF SUMMARY OF THE INVENTION

The present invention pertains to a stethoscope head with bell components having a wider rim than a conventional rim to provide for a better seal between the rim and the skin of the patient's body above the site to be auscultated. A non-metallic ring is disposed on the rim of the bell components and being flexible, allows the ring to adapt to the contours of the skin forming an effective seal. Further, the body of the bell components, being thicker than the conventional bell components, isolate the sound to be auscultated from the external noises. Moreover, the bell components are metallic providing for a better conductivity than those bell components that are non-metallic. However, metals are also good conductors of heat or cold. Therefore, in a hospital environment where it is typically air-conditioned, the bell component being in equilibrium with the surrounding temperature, becomes cold. The cold bell component, when applied to the skin of the patient's body, causes a chill to the patient that is discomforting. Non-metals, on the other hand, being good insulators, are poor conductors of heat or cold and do not cause a chill to the patient on contact. Accordingly, in the present invention, the ring, being non-metallic, is not as cold as would be with a metallic bell component having a metallic rim and no non-metallic ring, thereby, providing comfort to the patient on contact. Furthermore, the bell components are detachable providing for various of the described bell components to be attached to the stethoscope head depending on the particular use required.

Generally, a stethoscope includes a chest piece with a drum and a stem, the drum further having a diaphragm and a bell. Some chest pieces have detachable diaphragm structures and bell components. The diaphragm structures and bell components that attach to the drum of the chest piece are of various sizes so that the same chest piece can be used with infants, adults or areas with less exposed skin such as between the ribs or around the cervical area. The stem of the chest piece is normally connected to at least one tube through which sounds detected by the chest piece are transmitted. An ear piece is connected to the tube at the opposite end of the chest piece for receiving transmitted sounds.

It is appreciated that by providing a desirable acoustic seal between the rim of the bell components and the skin of the patient's body by using the wider rim and ring, auscultated sounds are better detected. Further, bell components being made of metal provides for better sound conductivity than those bell components that are non-metallic. Moreover, the thicker bell component body excludes the external noises from interfering with the sound to be detected. The non-metallic ring being not as cold as the metallic rim of the bell component, provides comfort to the patient upon contact. Other aspects and advantages of the invention will become apparent from the following more detailed description taken in conjunction with the accompanying drawings.

DETAILED DESCRIPTION OF THE INVENTION

From the description of the invention which follows it is understood that the stethoscope head illustrated in the figures is for the purposes of explanation only, and by no means limit the boundaries of the present invention. Further, it is understood that the stethoscope head used in describing the invention is merely done so to provide a thorough understanding of the present invention. It will be understood by one skilled in the art from reading the disclosure that the invention may be practiced on any type of stethoscopes available.

Figure 1:
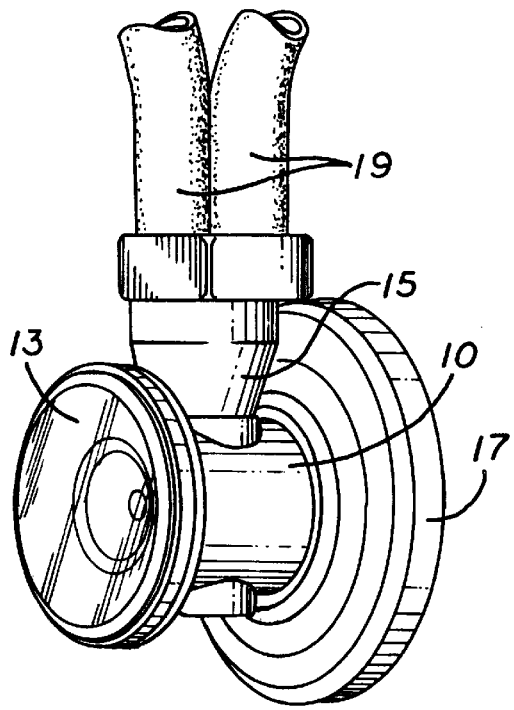
FIG. 1 illustrates a prior art stethoscope head with a large and small diaphragm structures.

FIG. 1 illustrates a prior art stethoscope head with a chest piece 10 and a small diaphragm 13 connected on one end of the chest piece 10 and a large diaphragm 17 connected to the other end of the chest piece. A valve stem 15 is embedded in the chest piece 10 to transmit the received auscultated sounds from the small diaphragm 13 or the large diaphragm 17 to the sound tubes 19.

Figure 2:
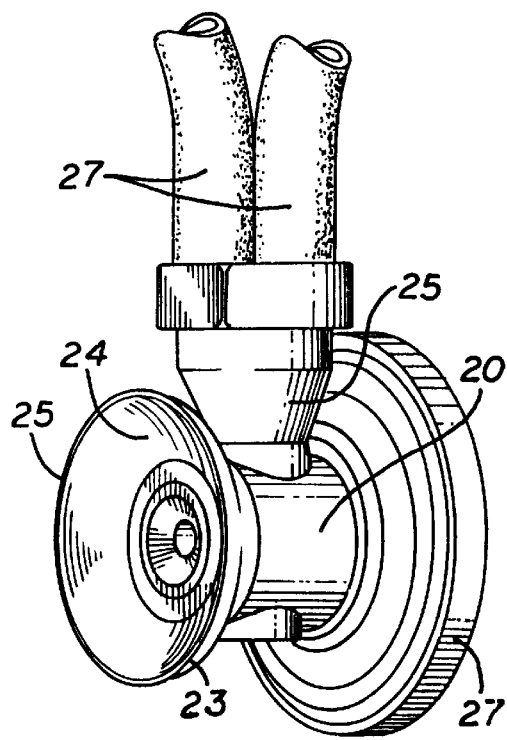
FIG. 2 illustrates another prior art stethoscope head showing a bell component with a conventional rim and a diaphragm structure behind the bell component.

FIG. 2 illustrates another prior art stethoscope head showing a conventional bell 23 with a rim 25. Here, the conventional bell is made of plastic, and therefore, is not a good conductor of auscultated sound. Another disadvantage is that the thin body 24 of the bell 23 does not effectively block out the external noise which interferes with the sound to be detected. In addition, the thin rigid rim 25 of the bell 23 does not provide the optimal seal between the bell 23 and the skin of the patient's body. The bell 23 is connected to one end of a chest piece 20 and a diaphragm 27 is connected to the other end of the chest piece 20. A valve stem 25 is embedded in the chest piece 20 to transmit the received auscultated sounds from the bell 23 or the diaphragm 27 to the sound tubes 29.

Figure 3:
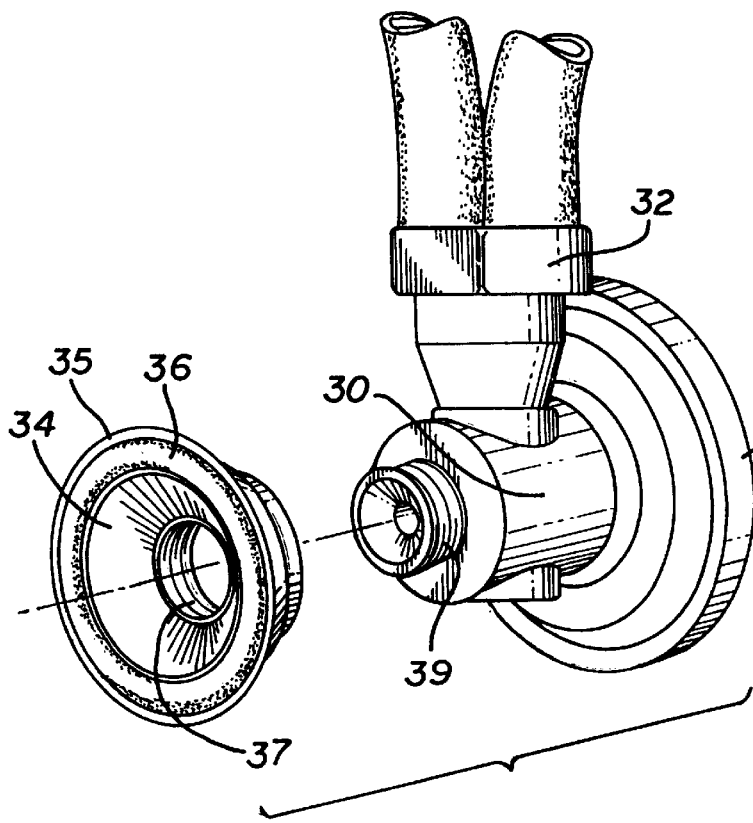
FIG. 3 illustrates an embodiment of the present invention showing a bell component with a wide rim and a non-metallic ring disposed on the rim. The figure further shows the detachable nature of the bell component allowing for various bell components to be attached depending on the particular use.

FIG. 3 illustrates an embodiment of the present invention. Here, an exemplary bell component 34 shows a rim 35 that is wider than the conventional rim 25 depicted in FIG. 2 to better acoustically seal the rim 35 to the skin of the patient's body above the site to be auscultated. The wide rim 35 allows a non-metallic ring 36 to be disposed on the rim 35 providing an effective seal between the rim 35 and the skin. Further, the bell component 34 is made of metal to provide for better sound conductivity than bell components that use a non-metallic material such as plastic, since metal conducts sound better than non-metals. However, metals are also good conductors of heat or cold. Therefore, in a hospital environment where it is typically air-conditioned, the bell component being in equilibrium with the surrounding temperature, becomes cold. The cold bell component, when applied to the skin of the patient's body, causes a chill to the patient that is discomforting. Non-metals, on the other hand, being good insulators, are poor conductors of heat or cold and does not cause a chill to the patient on contact. Accordingly, the non-metallic ring 36 disposed on the metal rim 35 insulates the metallic rim 35 from the patient providing comfort since metal is cold on contact whereas a non- metallic ring is not as cold.

In the preferred embodiment, the bell component 34 is detachable from the chest piece 30, as shown in FIG. 3, so that the bell component 34 can be replaced with other bell components depending on the patient's diagnostic needs. In this example, the bell component 34 is shown to be threaded onto the chest piece 30. The threaded portion 37 of the bell component 34 threadly engages the threaded portion 39 of the chest piece 30 until the bell component 34 is affixed to the chest piece 30. However, this is not the only method of affixing the bell component 34 to the chest piece 30 and other methods may be used. For example, the bell component 34 may be snapped onto the chest piece 30 using a snap lock similar to those used in milk bottle tops. In any case, the connection between the bell component 34 and the chest piece 30 must be tight preventing leaks that could interfere with the transmission of sounds. A valve stem 32 is embedded in the chest piece 30 and has a channel to transmit the received auscultated sounds from the bell 34 or the diaphragm 31 to the sound tubes 29. The valve stem 32 is rotatable to communicate with only one of the bell 34 or diaphragm 31 at a time.

Figure 4:
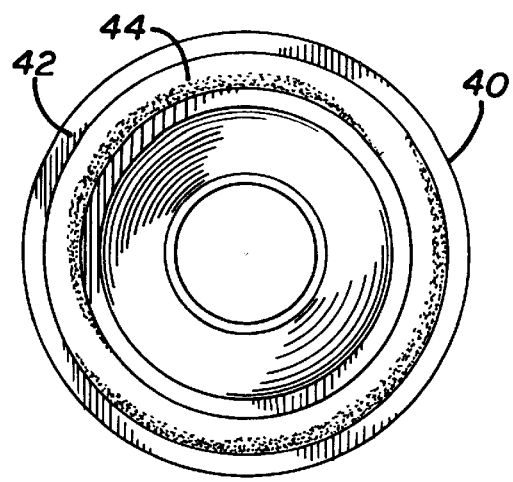
FIG. 4 illustrates the top view of the bell component showing the wide rim of the invention.
Figure 5:
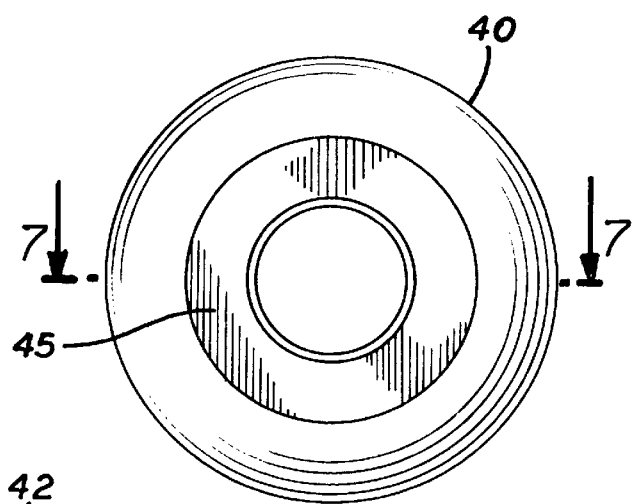
FIG. 5 illustrates the bottom view of the bell component.

FIG. 4 illustrates the top view of the bell component 40 showing the wide rim 42 and the embedded non-metallic ring 44 of the invention. The wide rim 42 and the wide non-metallic ring 44 provide for a desirable acoustic seal between the rim of the bell component 40 and the skin of the patient's body to be auscultated. The non-metallic ring 44 is flexible to adapt to the contour of the skin providing an effective seal from external noises that may interfere with the auscultated sound and may be made of rubber. However, any non-metallic material with similar flexibility may be used, for example, poly vinyl chloride (PVC) or foam sealed in cloth or PVC. FIG. 5 shows the bottom view of the bell component 40 including the portion 45 that adheres to the chest piece 30.

Figure 6:
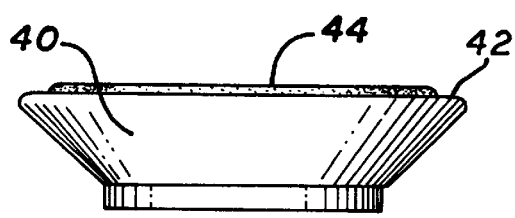
FIG. 6 illustrates a side view of the bell component showing the protruding non-metallic ring disposed on the rim.
Figure 7:
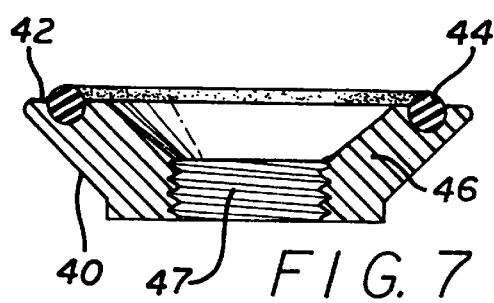
FIG. 7 illustrates a side cross sectional view of the bell component showing the wide rim and the embedded non-metallic ring on the rim of the bell component.
Figure 8:
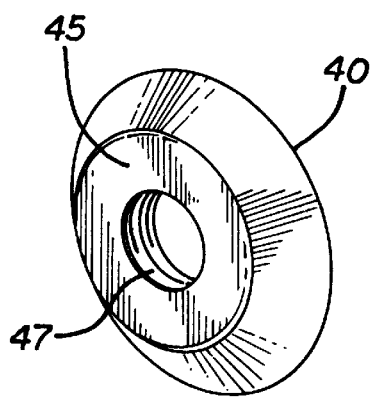
FIG. 8 illustrates a three dimensional view of the bell component.

FIG. 6 shows the side view of the bell component 40. It is appreciated that the nonmetallic ring 44 protrudes from the rim 42 of the bell component 40. Since the bell component 40 is metallic, the protruding non-metallic ring 44 insulates the metal rim 42 of the bell component 40 from the skin of the patient's body avoiding the discomfort of the coldness of metal when the bell component 40 makes contact with the skin. FIG. 7 is a cross sectional side view of the bell component 40 showing the non-metallic ring 44 disposed on the rim 42 of the bell component 40. The body 46 of the bell component 40 is thicker than the conventional body 24 of the bell component 23 described in FIG. 2 to further insulate the sound to be auscultated from the external noises. A clear view of the threads 47 is shown which threads onto the chest piece 30. FIG. 8 illustrates a three dimensional view of the bell component 40 showing the threads 47 and the portion 45 that adheres to the chest piece 30.

It will be appreciated that although an embodiment of the invention has been described in detail by way of example, modifications may be made without departing from the spirit and scope of the invention which should not be limited except as by the accompanying claims.

What is claimed:

1. A stethoscope head for detecting sounds, comprising:
   a chest piece having ends; one end adapted to receive one bell component selected from a plurality of bell components, said bell component selected according to an area to be auscultated;
   a valve stem having ends, disposed partially within said chest piece, so that one end of said valve stem is within said chest piece and at least one portion of said valve stem protrudes from said chest piece, each end of said valve stem in communication with the other end of said valve stem to transmit sound;
   said bell component for receiving sound coupled to one end of said chest piece and in communication with said valve stem within said chest piece, said bell component having a body and a rim; and
   a non-metallic ring disposed on said rim, said non-metallic ring protruding from said bell component.

2. The stethoscope head in claim 1, wherein said body of said bell component is adapted to exclude external noises from interfering with a sound to be auscultated.

3. The stethoscope head in claim 1, wherein said bell component is metallic.

4. The stethoscope head in claim 1, wherein said bell component is detachable.

5. The stethoscope head in claim 4, wherein said chest piece having a threaded portion on one end of the chest piece and said bell component having a second threaded portion such that said second threaded portion of said bell component is threadly engagable to said threaded portion of said chest piece.

6. The stethoscope head in claim 1, wherein said ring is flexible to adapt said ring to the contours of the skin above the site to be auscultated.

7. The stethoscope head in claim 1, wherein said ring is comprised of rubber.

8. The stethoscope head in claim 1, wherein said stethoscope head further comprises a diaphragm structure coupled to the other end of said chest piece and in communication with said valve stem within said chest piece to transmit sound and said valve stem being revolvable to communicate with one of said bell component and diaphragm structure.

9. The stethoscope head in claim 8, wherein said diaphragm structure is detachable.

10. The stethoscope head in claim 8, wherein said diaphragm structure is sized so as to be adapted to an area to be auscultated.

11. A plurality of detachable bell components adapted to be affixed to a chest piece of a stethoscope head, each bell component comprising:

a hollow body having openings on either end;

a rim on one end of said body sized so as to be adapted to an area to be auscultated;

a non-metallic ring disposed on said rim, said non-metallic ring protruding from said bell component.

12. The bell component in claim 12, wherein said body is adapted to exclude external noises from interfering with a sound to be auscultated.

13. The bell component in claim 12, further comprising means for affixing said other end of said bell component to said chest piece.

14. The bell component in claim 14, wherein said affixing means is a threaded portion adapted to engage a second threaded portion on said chest piece.

15. The bell component in claim 11, wherein said bell component is metallic.

16. The bell component in claim 11, wherein said ring is flexible to adapt said ring to the contours of the skin above the site to be auscultated.

17. The bell component in claim 11, wherein said ring is comprised of rubber.

\* \* \* \* \*

UNITED STATES PATENT AND TRADEMARK OFFICE
CERTIFICATE OF CORRECTION

PATENT NO. : 6,015,024
DATED : January 18, 2000
INVENTOR(S) : Rashman et al.

Page 1 of 1

It is certified that error appears in the above-identified patent and that said Letters Patent is hereby corrected as shown below:

<u>Column 4,</u>
Line 12, delete "that the nonmetallic ring" and insert -- that the non-metallic ring --.

<u>Column 6,</u>
Line 3, delete "in claim 12," and insert -- in claim 11, --.
Line 6, delete "in claim 12," and insert -- in claim 11, --.
Line 9, delete "in claim 14," and insert -- in claim 13, --.

Signed and Sealed this

Twenty-first Day of August, 2001

*Attest:*

*Attesting Officer*

NICHOLAS P. GODICI
*Acting Director of the United States Patent and Trademark Office*